United States Patent [19]

Kasat

[11] Patent Number: 5,102,656
[45] Date of Patent: Apr. 7, 1992

[54] ANTIPERSPIRANT CREAMS

[75] Inventor: Radhakrishna B. Kasat, Belle Mead, N.J.

[73] Assignee: The Mennen Company, Morristown, N.J.

[21] Appl. No.: 795,506

[22] Filed: Nov. 6, 1985

Related U.S. Application Data

[63] Continuation of Ser. No. 518,384, Jul. 29, 1983, abandoned.

[51] Int. Cl.$^5$ .......................... A61K 7/32; A61K 7/34
[52] U.S. Cl. ................................... 424/66; 424/68
[58] Field of Search ........................................... 424/66

[56] References Cited

U.S. PATENT DOCUMENTS

| | | | |
|---|---|---|---|
| Re. 21,406 | 3/1940 | Vogt | 62/114 |
| 1,783,864 | 12/1930 | Vogt | 62/114 |
| 2,087,161 | 7/1937 | Moore | 424/67 |
| 2,751,328 | 6/1956 | Sanders | 424/49 |
| 3,725,540 | 4/1973 | Wahl | 424/46 |
| 3,733,403 | 5/1973 | Chen | 424/83 |
| 3,924,004 | 12/1975 | Chang | 424/358 |
| 4,049,792 | 9/1977 | Elsnau | 424/66 |
| 4,083,956 | 4/1978 | Shelton | 424/66 |
| 4,126,679 | 11/1978 | Davy | 424/66 |
| 4,127,650 | 11/1978 | Buehler | 424/184 |
| 4,151,272 | 4/1979 | Geary | 424/68 |
| 4,265,878 | 5/1981 | Keil | 424/68 |
| 4,280,994 | 7/1981 | Turney | 424/68 |
| 4,331,609 | 5/1982 | Orr | 424/66 |

OTHER PUBLICATIONS

Chemetron Corp. Bulletin V300 "Votator Scraped Surface Heat Exchangers".

Primary Examiner—Dale R. Ore
Attorney, Agent, or Firm—Davis, Hoxie, Faithfull & Hapgood

[57] ABSTRACT

The invention is directed to a creamy, heterogeneous anhydrous antiperspirant product and to a method for making it. The product of the invention comprises essentially a volatile silicone product as a carrier, a gelling agent and a physiologically acceptable antiperspirant agent. Optional ingredients which can be included comprise surfactants, emollients, fillers, fragrances, coloring agents and the like. The method of the invention comprises mixing and heating the ingredients to a temperature above the melting point of the gelling agent, then cooling while mixing thoroughly to a temperature below the normal solidification point of the product.

19 Claims, 1 Drawing Sheet

ANTIPERSPIRANT CREAMS

This is a continuation of co-pending application Ser. No. 518,384, filed on July 29, 1983, now abandoned.

This invention is directed to a creamy, heterogeneous, anhydrous antiperspirant product and a method for making it.

Antiperspirant compositions in the form of creams have heretofore been primarily oil-in-water or water-in-oil emulsions. Though these provide convenient vehicles for carrying and delivering the astringent, emulsions generally tend to produce undesirable sensations on the skin, such as a sticky, wet feeling.

Anhydrous antiperspirant creams essentially comprising a liquid organic emollient material, an inorganic clay thickening/suspending agent, a gel-promoting agent and an astringent are also known. See Shelton U.S. Pat. No. 4,083,956. These also tend to produce undesirable sensations on the skin, will tend to remain on the skin and will cause stains on fabrics which come into contact with the product.

Antiperspirant stick products are also well-known in the prior art. Davy et al. U.S. Pat. No. 4,126,679, for example, describes antiperspirant stick products made by suspending an astringent in a solid solution of volatile silicones and long chain alcohols.

Prior art methods for preparing antiperspirant compositions tend to vary depending on whether the desired product is a stick or a cream. Shelton U.S. Pat. No. 4,083,956, for example, describes a method of preparing the thixotropic creams described there. In the described method of preparation, the emollient and optional ingredients soluble therein are mixed together. The clay suspending/thickening agent is added and mixed with an agitator to provide a uniform composition. Gel-promoting and anti-syneresis agents then are added until gellation occurs. At that point, antiperspirant active ingredients are blended into the mixture and uniformly dispersed. Apparently, no heating of the ingredients is necessary or desirable to prepare the Shelton products.

Davy et al. U.S. Pat. No. 4,126,679 and Elsnau U.S. Pat. No. 4,049,792 describe methods for making the antiperspirant sticks described there. Briefly, the ingredients are mixed together and melted, the astringent is added and intermixed and the resulting uniform product is poured into the stick form, at a temperature which is above the normal solidification point, and is allowed to cool to the normal solidification point of the product, and further to room temperature, without further agitation or mixing.

It has now been found, quite unexpectedly, that a more acceptable, efficacious, creamy antiperspirant product than those heretofore available or known may be made in accordance with the invention of the present application. The product of the invention provides a drier feeling than the prior art antiperspirant creams, imparts no sticky feeling whatever and does not cool the skin, as the prior art products do, after being applied thereto. Furthermore, it appears that the method employed in making the antiperspirant creams of the present invention is unexpectedly suitable to make the creams described herein. This invention is directed to a creamy, heterogeneous, anhydrous antiperspirant composition comprising the following essential ingredients: about 30 to about 70% (all percentages are by weight of total product) of a volatile silicone product as a carrier, about 7 to about 30% of a suitable gelling agent or agents, and about 12 to about 30% of a physiologically acceptable antiperspirant agent. This invention is also directed to a method of making the product of the invention.

The carrier, for example, can be any volatile, low viscosity silicone product, either cyclic or open-chain, or combinations thereof.

The gelling agent can be any of a number of compositions, including, for example, hydrogenated vegetable oil, hydrogenated castor oil, fatty acids, beeswax, paraffin wax, fatty alcohols, polyethylene and the like, or combinations thereof.

The antiperspirant agent can be any of the usual types of astringents, such as aluminum chlorohydrate, aluminum zirconium chlorohydrate, or the like.

Apart from the above-identified ingredients, i.e., the carrier, the gelling agent and the antiperspirant agent, it is desirable to include one or more optional ingredients in the creamy antiperspirant product of the invention. These optional ingredients together can comprise up to about 25% of the total product.

Useful optional ingredients include surfactants, fillers, emollients, fragrances and coloring agents, for example.

Surfactants can comprise up to about 5% of the total product and aid in preventing stains on clothing and in washing out any stains which do form.

Fillers can comprise up to about 20% of the total product and are normally less costly than the essential components of the product, thus reducing the overall cost.

Emollients can comprise up to about 15% of the total product, and, though not essential ingredients, are useful particularly when hydrogenated castor oil (also known as castor wax) is used as the gelling agent.

Fragrances can comprise up to about 1% of the total product.

Coloring agents can be added as desired.

The method of the invention comprises, very briefly, heating and thoroughly mixing all ingredients, then cooling the resultant mixture below the normal solidification point thereof, while subjecting the product to continuous shearing, agitation or mixing action. This process produces the creamy heterogeneous, anhydrous antiperspirant product of the invention. In practice, it has been found that a commercially available device called a Votator Scraped Surface Heat Exchanger, available from several sources, for example, Chemetron Corporation of Louisville, Ky., is useful, but not necessary, in practicing the method of the invention.

FIG. 1 illustrates in block diagram form, the process of the present invention, which will be more fully described below.

DETAILED DESCRIPTION

Figure 1:
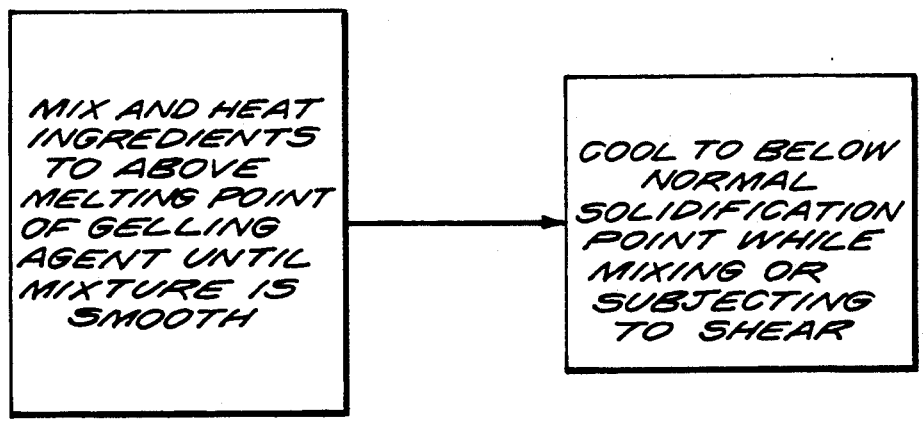

As stated above, one essential ingredient of the invention is a carrier, which comprises a volatile silicone product. The preferred volatile silicone products according to the invention are in general polydimethylcyclosiloxanes having 3 to 6 silicon atoms and linear polydimethyl siloxanes having a viscosity of not more than 10 centistokes at 25° C.

Such products are commercially available from several manufacturers and include the tetrameric and pentameric dimethyl cyclosiloxanes (also known as cyclomethicones) having the structures:

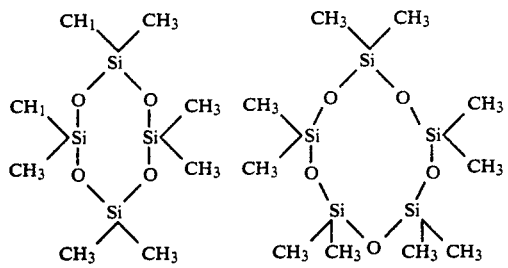

as well as linear compounds such as hexamethyl disiloxane $(H_3C)_3Si—O—Si(CH_3)_3$. The carrier comprises about 30 to about 70% of the total product, and preferably about 45 to about 65%. The carrier of choice is cyclomethicone, which is a polydimethylcyclosiloxane.

The gelling agent is another essential ingredient of the invention, comprises about 7 to 30% of the total product, and preferably about 7 to about 20%. Useful gelling agents include fatty alcohols having from 14 to 24 carbon atoms, hydrogenated castor oil, hydrogenated vegetable oil, fatty acids having from 14 to 36 carbon atoms, fatty acid ethylene glycol esters, glyceryl tribehenatee, beeswax, paraffin wax Polyethylene and the like. These gelling agents are available from many well-known chemical companies, including Emery, Caschem Inc., Procter & Gamble, Croda, Allied Chemical and the like.

The gelling agent of preference is a combination of stearyl alcohol and hydrogenated castor oil, which is available as Castorwax MP-70 from Caschem. Castorwax MP-80 is a useful substitute for the MP-70.

The physiologically acceptable antiperspirant agent is the third essential ingredient of the invention, comprises about 12 to about 30% of the total product and preferably about 18 to about 25%.

Antiperspirant compositions of necessity contain an effective antiperspirant agent. The number and composition of these agents is controlled in the United States by the Food and Drug Administration and the number of proposed agents is currently rather limited. They are in general aluminum or aluminum-zirconium salts or complexes. See 47 Federal Register 36504, Aug. 20, 1982. They include aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, aluminum zirconium trichlorohydrate GLY. See CTFA Cosmetic Ingredient Dictionary, Third Edition, pp. 10–13, 279.

The term "physiologically acceptable" is used to mean a material which may be used in cosmetic-drug preparations for external use without violation of the appropriate regulations of the United States Food and Drug Administration.

The preferred physiologically acceptable antiperspirant agent is aluminum chlorohydrate. A suitable alternative for this is aluminum zirconium tetrachlorohydrex GLY (hereafter "Al—Zr TC GLY"). These agents are powders and have a preferred particle size of about 1 to about 100 microns.

Useful optional ingredients include surfactants which, when present, can comprise up to 5% of total product, and preferably about 2%. Useful surfactants will have hydrophilic-lipophilic balances (HLB) of about 10 to about 20. Nonionic surfactants with HLBs of 12-20 are preferred. The commercially available surfactant of choice is Arlacel-165, which is a mixture of glyceryl stearate and polyethylene glycol 100 stearate. Other useful surfactants are those of the Tween series (ethoxylated sorbitol monoesters having different degrees of ethoxylation to provide different HLBs), the Myrj series, the Brij series and the Atlas series. All of these surfactants are commercially available from ICI United States and are well known.

Other useful optional ingredients are fillers, which, when present, can comprise up to about 20% of the total product and preferably about 10%. Useful fillers include talc, aluminum stearate, aluminum tristearate, zinc stearate, calcium carbonate, calcium stearate and the like. Talc is preferred.

Other useful optional ingredients are emollients, which, when present, can comprise up to about 15% of the total product and preferably about 8%. An emollient is particularly useful when hydrogenated castor oil is used as the gelling agent or one of the gelling agents. The preferred emollient is Fluid AP, which is commercially available and comprises the condensation product of about fourteen moles of propylene oxide with one mole of butanol (also known as polypropylene glycol 14 butyl ether).

Other useful optional ingredients are fragrances, which, when present, can comprise up to about 1% of the total product, and preferably about 0.5%.

Coloring agents are well known optional ingredients which may also be present in amounts of less than about 0.1%.

The following formulations exemplify the creamy products of the invention all percentages being by weight of total product:

|  | Formulation | | |
| Ingredient | 1 | 2 | 3 |
| --- | --- | --- | --- |
| Cyclomethicone | 52.5 | 54.0 | 59.80 |
| Stearyl alcohol | 24.0 | 7.2 | 6.25 |
| Castorwax MP-70 | 0.0 | 4.7 | 4.10 |
| Aluminum Chlorohydrate | 22.0 | 0.0 | 0.00 |
| Al—Zr TC GLY | 0.0 | 22.0 | 19.15 |
| Arlacel-165 | 1.0 | 1.0 | 1.00 |
| Fluid AP | 0.0 | 5.0 | 4.35 |
| Talc | 0.0 | 5.6 | 4.85 |
| Fragrance | 0.5 | 0.5 | 0.50 |

The method of the present invention comprises mixing and heating all ingredients except the fragrance, if any, to a temperature about the melting point of the gelling agent, cooling (while the mixing is continued) to approximately 55°–65° C., adding the fragrance, if any, while continuing to mix, then cooling further (while still mixing or agitating the product, or subjecting it to shear) to a temperature below the normal solidification point of the product, which is approximately in the range 44°–52° C., for the indicated composition ranges. The product preferably is then charged into the push-up type applicators described more fully below, and is allowed to come to room temperature. The above method can be performed by hand using suitable heaters, mixers and cooling baths, etc. The term "normal solidification point" as used herein means that temperature at which the product, when cooled without mixing or shearing, will ordinarily solidify to a block-type product.

In performing the method of the invention, it is preferred to use a commercial heat exchanger-mixer known as a Votator Scraped Surface Heat Exchanger to perform the step of cooling the product below the normal solidification point. This device is described more fully in bulletins available from one of the manufacturers, Chemetron Corporation, such as Bulletin V300. This device provides a very simple means for continuous thorough mixing of the product while it is being cooled to the desired temperature.

As will be readily apparent to those skilled in the art, the normal solidification point of the products of the invention will vary depending upon the actual carriers and gelling agents employed, and the amounts used of each.

It is believed that the method of the invention prevents the product from forming a solid matrix at its normal solidification point by continuous thorough mixing of the product as it cools to and below its normal solidification point. The product thus produced is a creamy heterogeneous, anhydrous antiperspirant suitable for packaging in jars or tubes. Another suitable package, and that preferred for the products of the invention, is a push-up type applicator, i.e., a tubular container having a piston advanced by a screw mechanism operated at the base thereof. The top of the tube may be closed by a perforated cap, with a cover being provided to seal the cap when not in use. Advance of the piston squeezes some of the product through the perforations onto the cap, whence it can be applied to the underarm. Such a device is more fully described in a copending, commonly assigned patent application of Richard T., Murphy, U.S. Ser. No. 400,885, filed July 22, 1982, now abandoned.

It has also now been found that when the products of the invention are produced using the method of the invention, the products are creamy and do not readily separate. When the Standard Test Method for Cone Penetration of Petrolatum (ASTM D937-77) is performed on the products of the invention, the products exhibit a penetration value of about 10 to about 36 mm. That standard method is hereby incorporated by reference. Preferably, the products will exhibit a value of about 12 to about 20 mm.

When the same combinations of ingredients as those of the invention are prepared but are allowed to cool to below the normal solidification points without continuous agitation or mixing, the cone penetration values are much lower, namely, in the range of about 2 to about 8 mm.

What is claimed is:

1. A heterogeneous, anhydrous antiperspirant cream comprising essentially about 30 to about 70% by weight of a volatile silicone product carrier, about 7 to about 30% of a gelling agent and about 12 to about 30% of a physiologically acceptable antiperspirant agent, and having a cone penetration value of about 10 to about 36 mm.

2. The cream of claim 1 wherein the carrier is a mixture of polydimethylcyclosiloxanes having 3 to 6 silicon atoms, the gelling agent is a combination of stearyl alcohol and hydrogenated castor oil and the physiologically acceptable antiperspirant agent is aluminum chlorohydrate or aluminum zirconium tetrachlorohydrex GLY.

3. The cream of claim 1 which additionally comprises up to 5 % of a nonionic surfactant having HLB values of about 10 to about 20.

4. The cream of claim 3 wherein the surfactant is a mixture of glyceryl stearate and polyethylene glycol 100 stearate.

5. The cream of claim 1 which additionally comprises up to about 155 of an emollient.

6. The cream of claim 5 wherein the emollient is polypropylene glycol 14 butyl ether.

7. The cream of claim 1 wherein the volatile silicone product carrier comprises about 45 to about 65% of the total product.

8. The cream of claim 1 wherein the gelling agent comprises about 7 to about 20% of the total product.

9. The cream of claim 1 wherein the physiologically acceptable antiperspirant agent comprises about 18 to about 25% of the total product.

10. A heterogeneous, anhydrous antiperspirant cream consisting of about 45 to about 65% by weight of a volatile silicone product carrier, about 7 to about 20% of a gelling agent and about 18 to about 25% of a physiologically acceptable antiperspirant agent.

11. The cream of claim 10 wherein the carrier is a mixture of polydimethylcyclosiloxanes having 3 to 6 silicon atoms.

12. The cream of claim 10 wherein the gelling agent is a combination of stearyl alcohol and hydrogenated castor oil.

13. The cream of claim 10 wherein the physiologically acceptable antiperspirant agent is aluminum chlorohydrate or aluminum zirconium tetrachlorohydrex GLY.

14. The cream of claim 10 which additionally includes up to 2% of a nonionic surfactant having HLB values of about 10 to about 20.

15. The cream of claim 14 wherein the surfactant is a mixture of glyceryl stearate and polyethylene glycol 100 stearate.

16. The cream of claim 12 which additionally includes up to about 8% of an emmolient and has a cone penetration value of about 10 to about 36 mm.

17. The cream of claim 16 wherein the emollient is polypropylene glycol 14 butyl ether.

18. A method of making a heterogeneous, anhydrous antiperspirant cream comprising the steps of mixing and heating the carrier, the gelling agent and the antiperspirant agent to a temperature above the melting point of the gelling agent, and cooling while the mixing is continued to a temperature below the normal solidification point of the product.

19. A method of making a fragrant antiperspirant cream comprising the steps of mixing and heating the carrier, the gelling agent, the antiperspirant agent and any optional ingredients except the fragrance to a temperature above the melting point of the gelling agent, cooling (while the mixing is continued) to approximately 55°-65° C., adding the fragrance while continuing to mix, then cooling further while still mixing the product to a temperature below the normal solidification point of the product.

* * * * *